United States Patent
Drevets et al.

(10) Patent No.: US 10,213,444 B2
(45) Date of Patent: Feb. 26, 2019

(54) COMPOSITION AND METHOD FOR TREATING BIPOLAR DISORDER

(71) Applicant: LAUREATE INSTITUTE FOR BRAIN RESEARCH, Tulsa, OK (US)

(72) Inventors: Wayne Curtis Drevets, Newton, PA (US); William Robert Yates, Tulsa, OK (US); Jonathan Bradley Savitz, Tulsa, OK (US); Sheldon H. Preskorn, Wichita, KS (US)

(73) Assignee: Laureate Institute For Brain Research, Tulsa, OK (US)

( * ) Notice: Subject to any disclaimer, the term of this patent is extended or adjusted under 35 U.S.C. 154(b) by 0 days.

(21) Appl. No.: 15/532,851

(22) PCT Filed: Dec. 4, 2015

(86) PCT No.: PCT/US2015/064106
§ 371 (c)(1),
(2) Date: Jun. 2, 2017

(87) PCT Pub. No.: WO2016/090316
PCT Pub. Date: Jun. 9, 2016

(65) Prior Publication Data
US 2017/0354667 A1      Dec. 14, 2017

Related U.S. Application Data

(60) Provisional application No. 62/087,468, filed on Dec. 4, 2014.

(51) Int. Cl.
*A61K 31/65* (2006.01)
*A61K 9/48* (2006.01)
*A61K 45/06* (2006.01)
*A61K 31/616* (2006.01)
*A61K 31/192* (2006.01)

(52) U.S. Cl.
CPC .............. *A61K 31/65* (2013.01); *A61K 9/48* (2013.01); *A61K 31/192* (2013.01); *A61K 31/616* (2013.01); *A61K 45/06* (2013.01); *A61K 9/4841* (2013.01)

(58) Field of Classification Search
None
See application file for complete search history.

(56) References Cited

U.S. PATENT DOCUMENTS

2005/0037983 A1     2/2005   Dinan et al.

OTHER PUBLICATIONS

Savitz J, Preskom S, Teague TK, et al., "Minocycline and aspirin in the treatment of bipolar depression: a protocol for a proof-of-concept, randomised, doubleblind, placebo-controlled, 2×2 clinical trial", BMJ Open 2012 , 2:e000643, pp. 1-14.
"Panel, Mini-panel, and Study Group Summaries from ACNP 53rd Annual Meeting", Neuropsychopharmacology (2014)40, S1-S111.
E. Fuller Torrey, John M. Davis, "Adjunct Treatments for Schizophrenia and Bipolar Disorder: What to Try When You Are Out of Ideas", Clinical Schizophrenia & Related Psychoses Jan. 2012, pp. 208-216C.

*Primary Examiner* — Brian J Davis
(74) *Attorney, Agent, or Firm* — McAfee & Taft

(57) ABSTRACT

Disclosed is a composition suitable for oral administration and capable of treating individuals suffering from unipolar disorder, bipolar disorder and/or bipolar disorder with an unhealthy body weight. The composition comprises a combination therapy of minocycline and acetylsalicylic acid delivered in doses that improve metabolic function and/or exert immune-modulating and/or anti-inflammatory effects. Also disclosed is a method for treating individuals suffering from the indicated disorders.

13 Claims, 5 Drawing Sheets

COMPOSITION AND METHOD FOR TREATING BIPOLAR DISORDER

This application claims priority to U.S. provisional application Ser. No. 62/087,468, filed on Dec. 4, 2014, the entirety of which is incorporated herein by reference.

TECHNICAL FIELD

The treatment of major depressive disorder, bipolar depression, the negative symptoms of schizophrenia, and depression secondary to general medical conditions remains a major challenge for psychiatry. The present disclosure provides improvements in compositions and methods for treating such conditions.

SUMMARY

The pharmaceutical composition of the present invention comprises a combination of a cyclooxygenase-1(COX-1) enzyme inhibitor and a compound capable of modulating the release of cytokines from microglial cells in the brain. For example, the combination comprises minocycline and acetylsalicylic acid (ASA, aspirin).

In another embodiment, the present invention provides a method for treating individuals suffering from bipolar disorder. Disclosed herein is a method for treating such individuals by the oral administration of a combination of a COX-1inhibitor and a compound capable of modulating the release of cytokines from microglial cells in the brain.

In another embodiment, the present invention provides a method for treating individuals suffering from bipolar disorder who are either treatment resistant or partial responders to first-line treatments. Disclosed herein is a method for treating such individuals by the oral administration of a combination of a COX-1inhibitor and a compound capable of modulating the release of cytokines from microglial cells in the brain. As used herein, treatment resistant means failure to respond to 2or more trials each using a different antidepressant drug administered at an adequate dose and over a sufficiently long duration to produce an antidepressant response. As used herein, partial responders to first line treatment means that following the most recent trial the CGI-I score (Clinical Global Impressions-Improvement scale) is greater than or equal to 3(encompassing the range of minimally improved, not improved or worsened) and the patient still meets DSM-V criteria for a current major depressive episode (i.e., as indicated by having either bipolar disorder—current or most recent episode depressed, or major depressive disorder—single or recurrent episode, along with the specifiers: partial remission, mild, moderate or severe).

In another embodiment, the present invention provides a method for treating individuals suffering from a combination of bipolar disorder and an unhealthy body weight. Individuals with a body mass index of greater than 25may be considered unhealthy if other factors such as metabolic abnormalities or excessive waist size are also present. Individuals with a body mass index greater than 30are considered obese, i.e. having an unhealthy body weight. Disclosed herein is a method for treating such individuals by the oral administration of a combination of a COX-1inhibitor and a compound capable of modulating the release of cytokines from microglial cells in the brain. For the purposes of this disclosure, individuals with a BMI greater than 25or satisfying the other criteria such as excessive waist size or metabolic abnormalities are referred to as having an "unhealthy body weight."

In another embodiment, the present invention provides a method for treating female patients suffering from bipolar disorder. Females have been shown to display more robust inflammatory responses to experimental endotoxin, show a different response profile to men after vaccination, and suffer from a greater incidence of autoimmune diseases, suggesting that this subgroup of patients may benefit more from immune-modulating treatments. Disclosed herein is a method for treating such individuals by the oral administration of a combination of a COX-1inhibitor and a compound capable of modulating the release of cytokines from microglial cells in the brain.

In another embodiment, the present invention provides a method for treating individuals suffering from a combination of bipolar disorder and inflammation. Individuals with bipolar disorder are considered to have inflammation if there is a co-occurring inflammatory medical condition or if factors such as elevations in inflammatory markers, including but not limited to pro-inflammatory cytokines, COX-1, COX-2, fibrinogen, CRP, white cell count, haptoglobin, ESR, oxidative stress markers, damage associated proteins (DAMPS) such as HMGB1, and neurotoxic kynurenine pathway metabolites such as quinolinic acid are present. Disclosed herein is a method for treating individuals having inflammation by the oral administration of a combination of minocycline and acetylsalicylic acid.

In another embodiment, the present invention provides a method for treating individuals suffering from major depressive disorder and/or dysthymia. Disclosed herein is a method for treating individuals having major depressive disorder and/or dysthymia by the oral administration of a combination of minocycline and acetylsalicylic acid.

DETAILED DESCRIPTION

Figure 1:
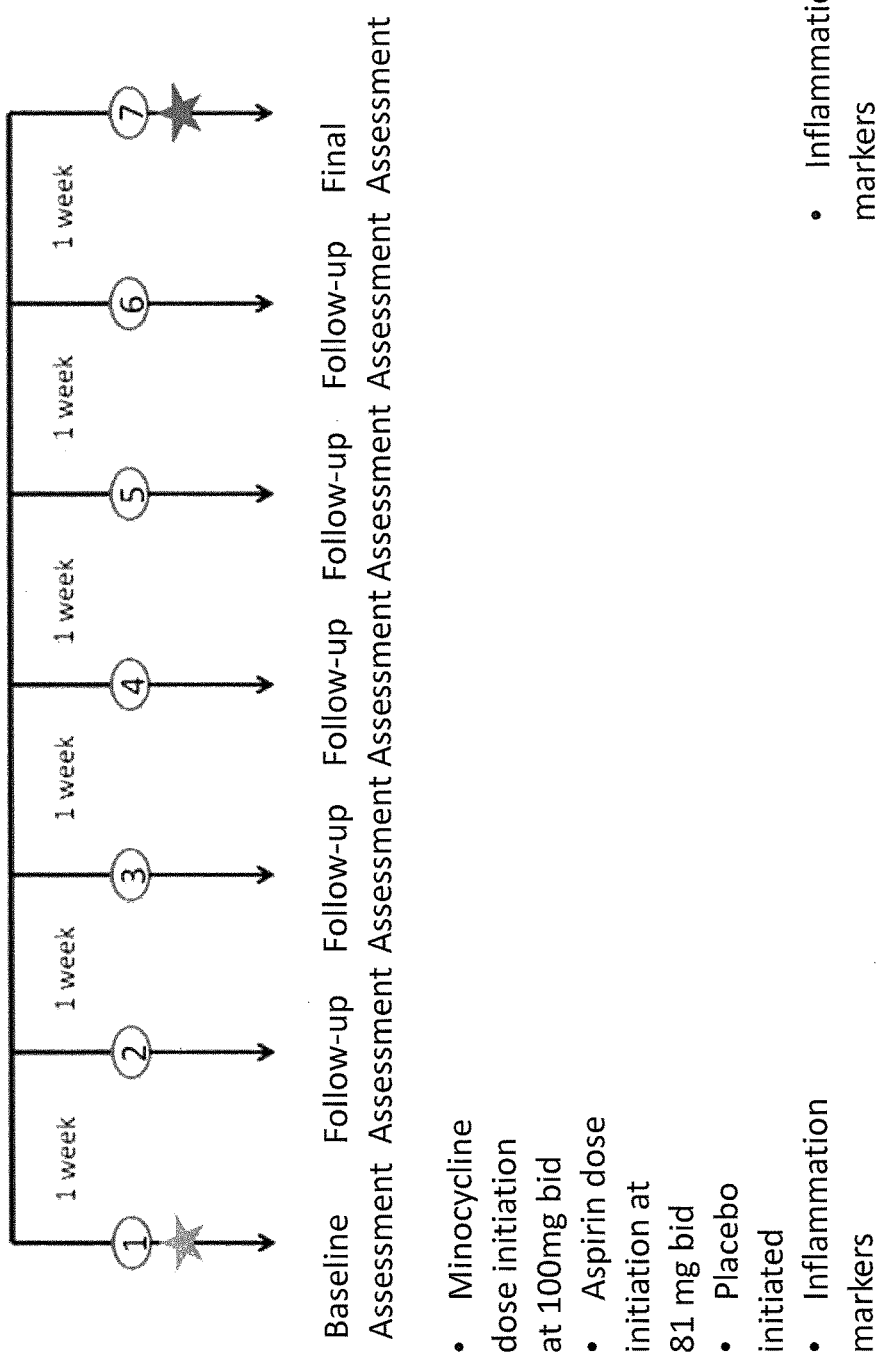
FIG. 1 depicts a double-blind, placebo-controlled trial of the use of the compounds disclosed herein to treat bipolar depression.

The pharmaceutical composition of the present invention comprises a combination of a COX-1inhibitor and a compound capable of modulating the release of cytokines from microglial cells in the brain. The compound capable of modulating the release of cytokines from the microglial cells is referred to herein as "cytokine modulator." The ratio of the dosage strength in mg of COX-1to cytokine modulator is from about 1:1to about 1:5.

Compounds suitable for inhibiting the activity of a COX-1enzyme and suitable for use in the pharmaceutical composition include, but are not necessarily limited to: acetylsalicylic acid (aspirin) and naproxen. Compounds suitable for modulating the release of cytokines from microglial cells in the brain and suitable for use in the pharmaceutical composition include, but are not necessarily limited to: minocycline, adalimumab, certolizumab, pegol, anakinra, rilonacept and canakinumab.

The pharmaceutical composition may also include compounds selected for their ability to allow the safe and effective formulation, packaging and delivery of a combination COX-1 inhibitor and cytokine modulator, for example, minocycline and aspirin. Such compounds include but are not necessarily limited to appropriate buffering and excipient agents.

The pharmaceutical composition may be in the form of a single dose drug delivery system combining the COX-1 inhibitor and cytokine modulator. Such single dose drug delivery system may be in the form of a pill or a capsule housing the compound capable of inhibiting a COX-1 enzyme and the compound capable of modulating the release of cytokines from microglial cells in the brain in a discrete form. Alternatively, the single dose drug delivery system may be in the form of a capsule containing the compound capable of inhibiting a COX-1 enzyme and the compound capable of modulating the release of cytokines from microglial cells in the brain in a homogeneous blend.

The method for treating individuals with the pharmaceutical composition comprises establishing the dosage necessary to achieve a pharmacological response. The dosage for the COX-1 inhibitor, i.e. the compound capable of inhibiting a COX-1 enzyme, will generally be from about 0.5 mg/kg of body weight to about 2 mg/kg of body weight. The dosage for the cytokine modulator, i.e. compound capable of modulating the release of cytokines from microglial cells in the brain, will generally be from about 1 mg/kg of body weight to about 6 mg/kg of body weight. When the COX-1 inhibitor is acetylsalicylic acid, the dosage will generally be from about 0.5mg/kg of body weight to about 2 mg/kg of body weight. When the cytokine modulator is minocycline, the dosage will generally be from about 1 mg/kg of body weight to about 6mg/kg of body weight. Both compounds will be taken by the individual at the same time as a single pill or as individual pills. Typically, the compounds will be taken in the morning and evening (BID). The compounds will generally be taken orally. However, other forms of administration are also suitable.

ASA is lipophilic and brain penetrant when administered orally with a brain to blood ratio of 0.32. Thus, the level of ASA within brain is 32% of the level within blood plasma.

Cytokine modulators such as minocycline have high lipophilicity enabling efficient transfer across the blood brain barrier. For example, when administered orally minocycline levels within cerebrospinal fluid typically fall within the range of about 11-56% of plasma concentrations. Thus, the level within cerebrospinal fluid is 11-56% of that found in blood plasma.

Minocycline inhibits the microglial-mediated release of proinflammatory cytokines IL-1β, TNF-α, IL-6, and p38, while promoting release of the anti-inflammatory cytokine, IL-10. Minocycline also inhibits matrix metalloproteinases thereby precluding processing of TNF-α and IL-1β cytokines such as into their biologically active forms. Minocycline also prevents glutamate-induced activation of nitric oxide synthase. As such minocycline acts as an effective scavenger of proapoptotic reactive oxygen species, such as nitric oxide, and protects against excitotoxicity. Nitric oxide facilitates glutamate release from presynaptic neurons and inhibits glial glutamate transporters, amplifying glutamatergic signaling, and contributing to excitotoxic cell death. Minocycline also upregulates a key molecular factor in the apoptosis pathway, B-cell CLL/lymphoma 2(BCL-2), that represses apoptosis induced by cytotoxic insults.

Using the Netherlands based PHARMO Record Linkage System, researchers tested whether NSAIDs or glucocorticoids would ameliorate bipolar symptoms. The main outcome measure was a calculated incidence density of medication events (change in the type or numbers of psychotropic medications prescribed, or increase [>30%] in the psychotropic drug dose). Individuals receiving lithium treatment who were additionally receiving low-dose (≤81 to 162 mg/day) aspirin were 17% less likely to have a medication event, while high-dose aspirin or non-selective NSAIDs, selective COX-2 inhibitors, and glucocorticoids instead were associated with an increase in medication events, suggesting destabilization of bipolar illness.

The above pharmaceutical compound comprising minocycline and acetylsalicylic acid was tested using a double-blind, placebo-controlled trial with a 2×2 design. The study examined subjects with bipolar disorder during a current major depressive episode ("bipolar depression"). Most subjects were either partial responders to existing antidepressant and/or mood stabilizing treatments or were treatment resistant. The subjects were randomized to receive either (1) placebo-minocycline plus placebo-acetylsalicylic acid, or (2) active-minocycline (100 mg b.i.d.) plus placebo-acetylsalicylic acid, or (3) placebo-minocycline plus active-acetylsalicylic acid (81 mg b.i.d.), or (4) active-minocycline (100 mg b.i.d.) plus active-acetylsalicylic acid (81 mg b.i.d.) (FIG. 1). Clinical symptoms of depression and mania were measured using the Montgomery-Asberg Depression Rating Scale (MADRS) and the Young Mania Rating Scale (YMRS), respectively.

The resulting experimental data shows that individuals with bipolar depression (notably females and individuals with a body mass index greater than 30) in the active-minocycline plus active-acetylsalicylic acid arm exhibited a greater response and remission rates compared with subjects in the double placebo group. For the data produced below, the treatment method for administering the combination of each composition, including the active-minocycline and active-acetylsalicylic acid, entailed the following steps: administer ASA 81 mg p.o b.i.d and minocycline 100 mg p.o b.i.d. As depicted in FIG. 1, each session number (total of 7) is encircled, with the timing between sessions indicated in weeks with a 2 business day window on either side of visit target date to complete the visit. Session 1 (far left) is the baseline and session 7 (far right) is the study end. The study duration is 6 weeks.

Of the 99 patients who were randomized, 87 started treatment and completed a sufficient number of sessions (at least 3 weeks of treatment) to be included in the last-observation carried forward analysis (LOCF) shown below. For these 87 subjects, 79 completed the entire study. Eight subjects dropped-out early, all from the active treatment groups— 4 from minocycline+ASA, 3 from ASA+placebo, and one from minocycline+placebo. Since existing anti-depressant medications generally begin to exert antidepressant effects within 3 weeks, in this trial, data from patients with at least 3 weeks of treatment were including in the LOCF analysis.

The randomization of subjects produced groups having similar demographic data and clinical baseline ratings at baseline, as shown in table 1. Table 1 provides results reflecting the mean demographic and clinical data at study entry of subjects who completed at least 3 weeks of treatment.

TABLE 1

| Group | ASA + Mino. | ASA + Pl. | Mino. + Pl. | Pl. + Pl. |
|---|---|---|---|---|
| Sample Size | 26 | 18 | 16 | 27 |
| Sex (% female) | 81 | 67 | 69 | 74 |
| Age | 40.3 ± 10.1 | 41.2 ± 10.1 | 44.6 ± 9.3 | 40.4 ± 10.7 |
| BMI | 30.8 ± 7.4 | 32.1 ± 7.4 | 31.5 ± 5.3 | 31.5 ± 10.3 |
| MADRS | 28.1 ± 5.4 | 25.3 ± 6.1 | 27.0 ± 4.1 | 28.9 ± 6.2 |
| YMRS | 4.8 ± 2.2 | 5.5 ± 3.5 | 3.3 ± 2.5 | 3.9 ± 2.6 |

Abbreviations:
ASA = acetylsalicylic acid;
BMI = Body Mass Index;
MADRS = Montgomery-Asberg Depression Rating Scale;
YMRS = Young Mania Rating Scale:
Mino. = minocycline;
Pl. = placebo.
The MADRS was declared a priori as the rating scale for assessing the primary outcome measure.

Table 2, below shows a comparison of the percentage of responders across the four treatment arms after a last observation carried forward (LOCF) analysis. Response to medication/placebo was defined as a greater than 50% reduction in MADRS scores between the baseline and final assessment. Table 2 provides results reflecting percentage of treatment responders by group, and relative risk reduction (RRR), absolute risk reduction (ARR) and, number needed to treat (NNT) for the combination ASA/minocycline treatment.

TABLE 2

| Group | ASA + Mino. | ASA + Pl. | Mino. + Pl. | Pl. + Pl. | RRR | ARR | NNT |
|---|---|---|---|---|---|---|---|
| Total sample size (n) | 26 | 18 | 16 | 27 | — | — | — |
| Percentage of responders | 58 | 56 | 38 | 41 | 42 | 17 | 6 |
| Percentage of responders (BMI >30) | 64 | 44 | 38 | 46 | 39 | 18 | 6 |
| Percentage of female responders | 62 | 50 | 55 | 35 | 77 | 27 | 4 |

Figure 2:
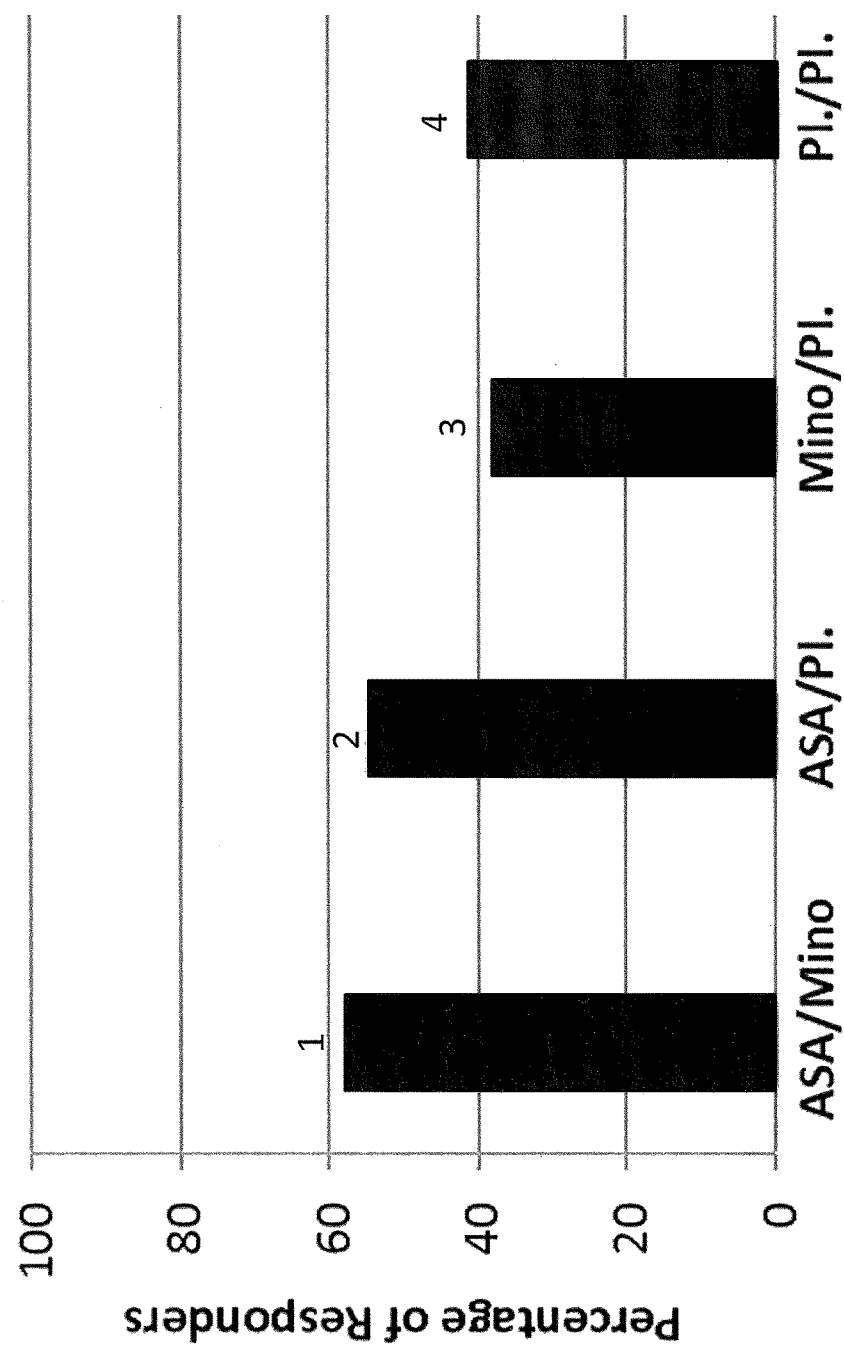
FIG. 2 depicts the mean difference in responders between the active treatment groups in the study.

As shown in FIG. 2, the group receiving combined minocycline and acetylsalicylic acid treatment had a greater percentage of responders to treatment (defined as 50% reduction in MADRS score) relative to the placebo group. Specifically, 58% of patients in the minocycline+ASA group versus 41% in the placebo group responded to treatment. This 17% difference in response rates corresponds to a number needed to treat (NNT) of approximately 6. Additionally, with reference to FIG. 3, when considering the subgroup of individuals with a body mass greater than 30, the improvement in MADRS score also is prominent with an 18% reduction in absolute risk corresponding to an NNT of 6. Additionally, with reference to FIG. 4, when considering female patients only, the improvement in MADRS score is substantial with a 27% reduction in absolute risk corresponding to an NNT of 4.

Figure 5:
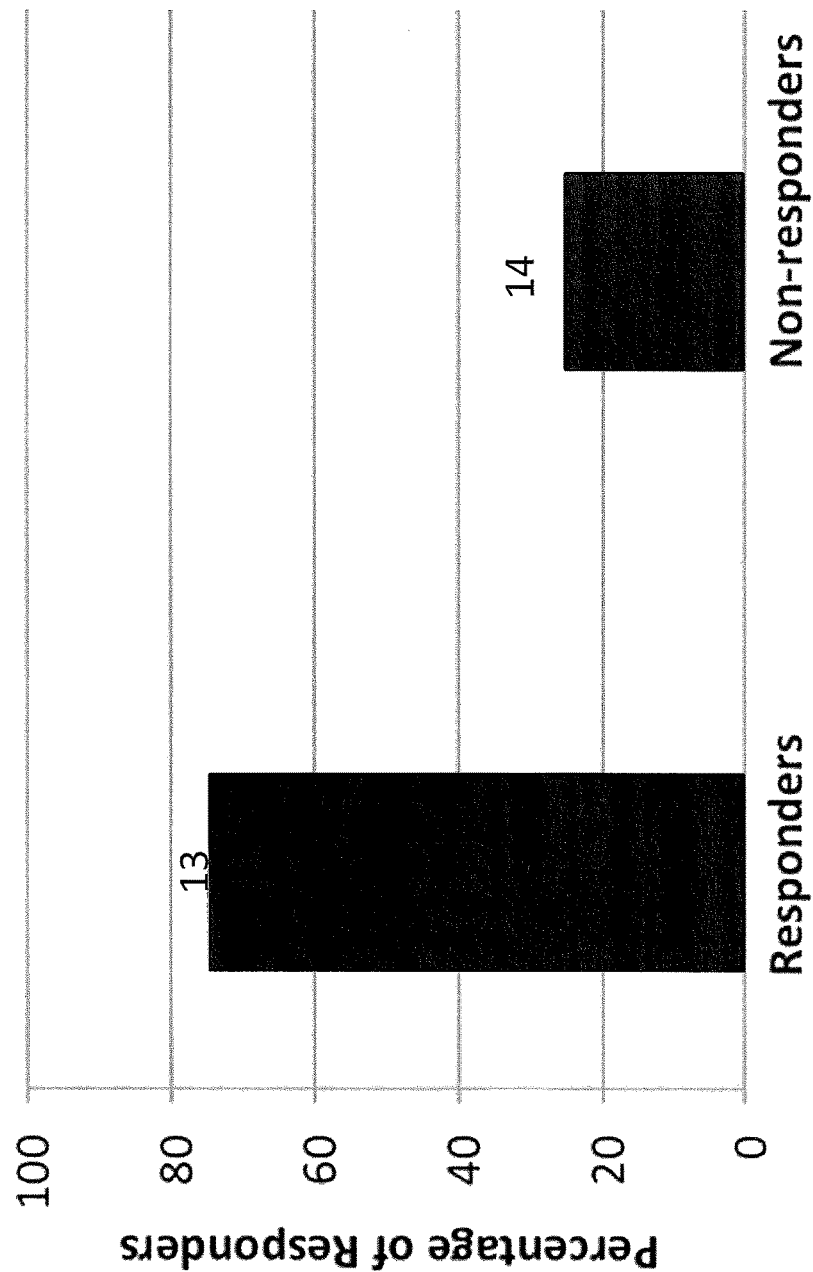
FIG. 5 depicts the mean percent of responders (column 13) and non-responders (column 14) to Minocycline+ASA in the subgroup of patients with major depressive disorder.

With reference to FIG. 5, patients who themselves had major depressive disorder (unipolar depression) and had a first-degree relative with bipolar disorder were allowed to participate in the study. In the subset of patients with major depressive disorder (n=10), 75% responded to the combination of minocycline+ASA (3/4) compared to 50% response in the minocycline+placebo group (1/2), and 0% in the ASA+placebo group (0/3). The data document that the combination of minocycline and ASA has effectiveness for the treatment of additional forms of non-bipolar depression such as major depressive disorder and dysthymia. In FIG. 5, column 13 reflects the mean percent of responders and column 14 reflects the non-responders.

Figure 3:
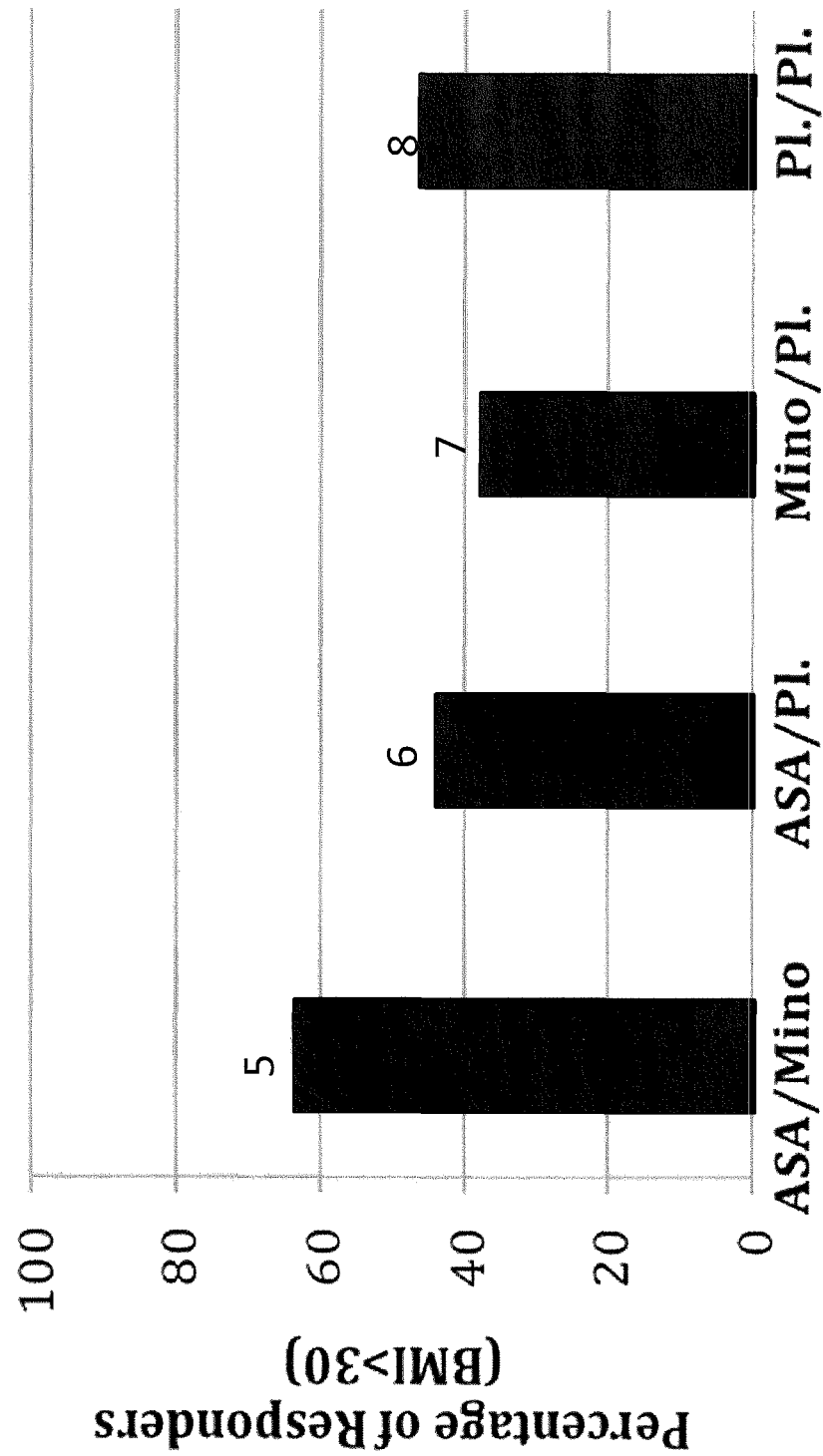
FIG. 3 depicts the mean difference in responders in the subset of patients with a body mass index (BMI) greater than 30.
Figure 4:
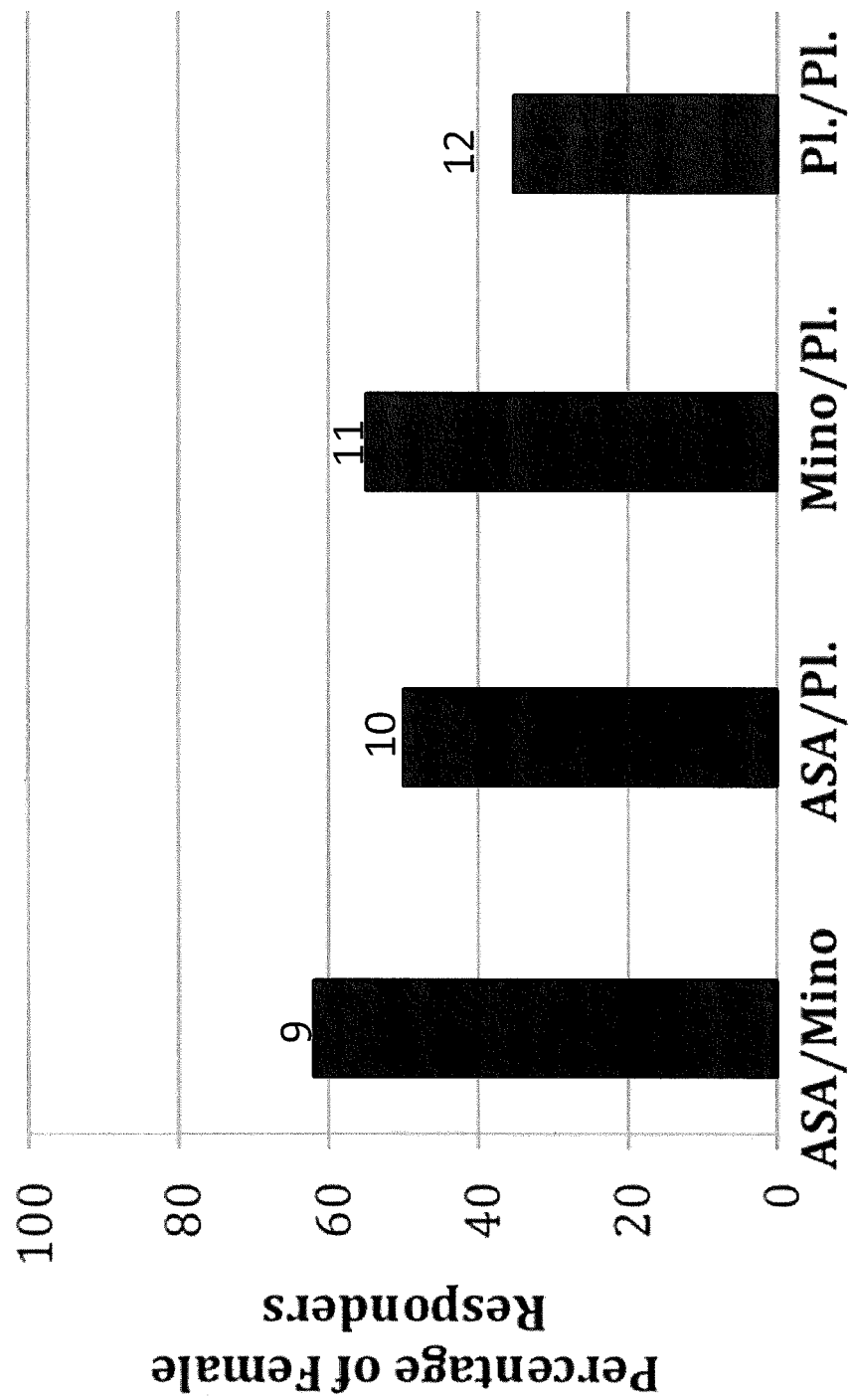
FIG. 4 depicts the mean difference in female responders across the treatment groups.

FIG. 2 depicts the mean percent difference in responders between the active treatment groups: ASA+minocycline (Column 1), ASA+placebo (column 2), and minocycline+placebo (column 3) versus the double placebo group (column 4). Response is conventionally defined as a greater than 50% decrease in scores on MADRS, the primary outcome measure. FIG. 3 depicts the mean percent difference in responders in the subset of the patients with a BMI>30 between the active treatment groups: ASA+minocycline (column 5), ASA+placebo (column 6), and minocycline+placebo (column 7) versus the double placebo group (column 8). FIG. 4 depicts the mean percent difference in female responders across the treatment groups: ASA+minocycline (column 9), ASA+placebo (column 10), and minocycline+placebo (column 11) versus the double placebo group (column 12).

In addition, in the full sample, the mean percent decrement in Young Mania Rating Scores (YMRS) scores was 38% for the minocycline+acetylsalicylic acid group, compared with 19% for the double placebo group. Thus, the combination of minocycline and acetylsalicylic acid appears to provide a mood stabilizing effect.

The foregoing discussion demonstrates the effectiveness of a combination therapy of a COX-1 inhibitor with cytokine modulator for the treatment of individuals suffering from bipolar depression. The therapeutic effect is most salient in patients with treatment resistance (or partial responders to first-line treatments), females, and patients with an unhealthy body weight. The foregoing discussion also demonstrates the effectiveness of a combination therapy of a COX-1 inhibitor with cytokine modulator for the treatment of individuals suffering from major depressive disorder. The foregoing disclosure is considered to be merely exemplary of the current invention. Other embodiments of the present invention will be apparent to one skilled in the art. As such, the foregoing description merely enables and describes the general uses and methods of the present invention. Accordingly, the following claims define the true scope of the present invention.

We claim:

1. A method for treating bipolar depression in an individual comprising:
   delivering, as a single drug delivery system, to an individual with bipolar depression a pharmacologically effective amount of a compound capable of inhibiting a COX-1 enzyme and a pharmacologically effective amount of a compound capable of modulating the release of cytokines from microglial cells in the brain.

2. The method of claim 1, wherein said single drug delivery system delivers from about 0.5 mg/kg of body weight to about 2.0 mg/kg of body weight of said pharmacologically effective amount of said compound capable of inhibiting a COX-1 enzyme.

3. The method of claim 1, wherein said single drug delivery system delivers from about 1 mg/kg of body weight to about 6 mg/kg of body weight of said pharmacologically effective amount of said compound capable of inhibiting a COX-1 enzyme to said individual.

4. The method of claim 1, wherein said method delivers said compound capable of inhibiting a COX-1 enzyme and said compound capable of modulating the release of cytokines from microglial cells in the brain to said individual twice a day.

5. The method of claim 1, wherein said method delivers said compound capable of inhibiting a COX-1 enzyme and said compound capable of modulating the release of cytokines from microglial cells in the brain to said individual once in the morning and once in the evening.

6. The method of claim 1 wherein said compound capable of inhibiting a COX-1 enzyme is selected from the group consisting of: acetylsalicylic acid and naproxen.

7. The method of claim 1, wherein said compound capable of modulating the release of cytokines from microglial cells in the brain is selected from the group consisting of minocycline, adalimumab, certolizumab, pegol, anakinra, rilonacept and canakinumab.

8. A method for treating bipolar depression in an individual comprising:
   delivering, as a single drug delivery system, to an individual with bipolar depression and a body mass index of greater than 25 a pharmacologically effective amount of a compound capable of inhibiting a COX-1 enzyme and a pharmacologically effective amount of a compound capable of modulating the release of cytokines from microglial cells in the brain.

9. The method of claim 8, wherein said single drug delivery system delivers from about 0.5 mg/kg of body weight to about 2.0 mg/kg of body weight of said pharmacologically effective amount of said compound capable of inhibiting a COX-1enzyme.

10. The method of claim 8, wherein said single drug delivery system delivers from about 1 mg/kg of body weight to about 6 mg/kg of body weight of said pharmacologically effective amount of said compound capable of inhibiting a COX-1 enzyme.

11. A method for treating bipolar depression in a female individual comprising:
   delivering, as a single drug delivery system, to a female individual with bipolar depression a pharmacologically effective amount of a compound capable of inhibiting a COX-1 enzyme and a pharmacologically effective amount of a compound capable of modulating the release of cytokines from microglial cells in the brain.

12. The method of claim 11, wherein said single drug delivery system delivers from about 0.5 mg/kg of body weight to about 2.0 mg/kg of body weight of said pharmacologically effective amount of said compound capable of inhibiting a COX-1enzyme.

13. The method of claim 11, wherein said pharmacologically effective amount of a compound capable of modulating the release of cytokines from microglial cells delivers from about 1 mg/kg of body weight to about 6 mg/kg of body weight to said individual.

* * * * *